United States Patent [19]

Tsuruoka et al.

[11] 4,264,532
[45] Apr. 28, 1981

[54] PROCESS FOR PREPARING D,L-2-AMINO-4-METHYLPHOSPHINOBUTYRIC ACID

[76] Inventors: Takashi Tsuruoka, Kawarachodanchi 14-833, 1 Kawaracho, Saiwai-ku, Kawasaki-shi, Kanagawa 210; Akira Suzuki, 17, Daikanyamacho 17 chome, Shibuya-ku, Tokyo 150; Kunitaka Tachibana, 6-1-1119, Isogo 3 chome, Isogo-ku, Yokohama-shi, Kanagawa 235; Kazuko Mizutani, 321, Hazawacho, Kanagawa-ku, Yokohama-shi, Kanagawa 221; Yasuharu Sekizawa, 2-4, Higashi 3 chome, Shibuya-ku, Tokyo 150; Shigeharu Inouye, 16, Tsutsujigaoka, Midori-ku, Yokohama-shi, Kanagawa 227; Tetsuo Takematsu, 612,, Minemachi Utsunomiya-shi, Tochigi 320, all of Japan

[21] Appl. No.: 140,198

[22] PCT Filed: Jun. 15, 1979

[86] PCT No.: PCT/JP78/00058

§ 371 Date: Jun. 15, 1979

§ 102(e) Date: Jun. 15, 1979

[87] PCT Pub. No.: WO79/00405

PCT Pub. Date: Jul. 12, 1979

[30] Foreign Application Priority Data

Dec. 19, 1977 [JP] Japan ............................ 52-151632

[51] Int. Cl.$^3$ ........................... C07F 9/32; C07F 9/30
[52] U.S. Cl. .................................. 260/968; 260/950; 260/502.5
[58] Field of Search ..................... 260/950, 502.5, 968

[56] References Cited

U.S. PATENT DOCUMENTS

| 2,631,162 | 3/1953 | Ladd et al. ........................... 260/950 |
| 2,664,438 | 12/1953 | Ladd et al. ........................... 260/950 |
| 2,971,019 | 2/1961 | Ladd et al. ........................... 260/950 |
| 3,832,394 | 8/1974 | Niida et al. ......................... 260/502.5 |

FOREIGN PATENT DOCUMENTS

| 130354 | 3/1978 | German Democratic Rep. ..... 260/950 |
| 49-13123 | 2/1974 | Japan .................................. 260/502.5 |

OTHER PUBLICATIONS

Gruszecka et al., "Chem. Abstracts" vol. 85, No. 1, (1976), p. 467, item 85:5777y.

*Primary Examiner*—Joseph E. Evans
*Attorney, Agent, or Firm*—Frishauf, Holtz, Goodman & Woodward

[57] ABSTRACT

This invention relates to a novel process for preparing D,L-2-amino-4-methylphosphinobutyric acid having herbicidal and antifungicidal activities which comprises subjecting acrolein to reaction with a dialkyl phosphonite to synthesize an acetal of an ester of 3-oxopropylmethylphosphinic acid; treating the thus obtained compound with an acid for deacetalization to obtain an ester of 3-oxopropylmethylphosphinic acid and then applying the Strecker's process used for amino synthesis to the thus obtained ester.

5 Claims, No Drawings

PROCESS FOR PREPARING D,L-2-AMINO-4-METHYLPHOSPHINOBUTYRIC ACID

FIELD OF TECHNOLOGY

This invention relates to a novel process for preparing D,L-2-amino-4-methylphosphinobutyric acid having herbicidal and antifungicidal activities.

BACKGROUND OF TECHNOLOGY

With regard to the compound of this invention, there has already been established by the present inventors a method for the synthesis thereof in which is used the reaction of an ester of 2-haloethylmethylphosphinic acid with an ester of acetoaminomalonic acid (Japanese Provisional Patent Publication No. 48-91019/1973). Further, H. Gross et al. established a method by which the compound was obtained via β-chloroethyl ester of β-chloroethylmethylphosphinic acid [J. Pract. Chem., 318, 157 (1976)], and P. Mastalerz et al. carried out a synthesis of the present compound by using a dialkyl methylphosphonite and a dialkyl acetal of a 3-halopropanal [Rocz. Chem., 49, 2127 (1975)].

DISCLOSURE OF INVENTION

As a result of further investigations on a more inexpensive process for preparing D,L-2-amino-4-methylphosphinobutyric acid, the present inventors have found an efficient process for the synthesis thereof in which is used acrolein as an inexpensive raw material, and accomplished this invention. Namely, the present inventors have established an industrially advantageous process for the synthesis of D,L-2-amino-4-methylphosphinobutyric acid by applying the Strecker's process to an ester of 3-oxopropylmethylphosphinic acid, which is a deacetalized form of an acetal of an ester of 3-oxopropylmethylphosphinic acid which is obtained by subjecting acrolein to reaction with a dialkyl methylphosphonite in a solvent such as an alcohol, a phenol, etc.

That is, an object of this invention is to provide a process for preparing the desired product, which is easily applicable industrially by using as a starting material, acrolein which is extremely available and inexpensive.

Other objects and advantages of this invention will be apparent by the following descriptions.

Next, the present invention will be explained in more detail.

Firstly, an acetal of an ester of 3-oxopropylmethylphosphinic acid represented by general formula (II):

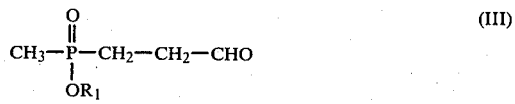

wherein $R_1$ means a lower-alkyl group having 1 to 5 carbon atoms and $R_2$ means a lower-alkyl group having 1 to 5 carbon atoms, an allyl group, a phenyl group or a substituted phenyl group, is obtained by subjecting a dialkyl methylphosphonite represented by general formula (I):

$$CH_3-P(OR_1)_2 \quad (I)$$

wherein $R_1$ has the same meaning as defined above to reaction with acrolein in a solvent of the general formula:

$$R_2OH$$

wherein $R_2$ has the same meaning as defined above.

As a solvent of the general formula: $R_2OH$, there are included an alkanol having 1 to 5 carbon atoms such as methanol, ethanol, etc; allyl alcohol; phenol; a substituted phenol; and so on.

The reaction may preferably be conducted under shielding of the light, in a stream of an inert gas such as nitrogen, carbon dioxide, etc., or in the presence of such a polymerization inhibitor as hydroquinone etc., since acrolein is unstable.

Since the present reaction is an exothermic one, the mixing of both starting materials is conducted at a temperature of $-50°$ to $0°$ C.; then the temperature is raised gradually; and finally, the reaction is conducted at $40°$ to $100°$ C. for 5 to 30 hours.

Subsequently, the thus obtained acetal of an ester of 3-oxopropylmethylphosphinic acid is subjected to reaction with an acid to carry out deacetalization (removing of acetal group) thereof, whereby is obtained an ester of 3-oxopropylmethylphosphinic acid represented by general formula (III):

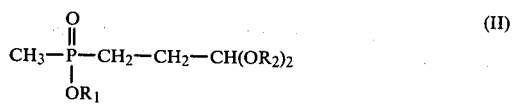

wherein $R_1$ has the same meaning as defined above the deacetalization reaction (removing of acetal group) is conducted in an aqueous solvent such as water, an aqueous acetone, an aqueous alcohol, an aqueous dioxane, an aqueous tetrahydrofuran, etc., in the presence of a mineral acid such as hydrochloric acid, sulfuric acid, etc., or an organic acid such as tartaric acid etc., preferably in a stream of an inert gas such as nitrogen etc., by the addition of a polymerization inhibitor such as hydroquinone etc., to the reaction system, taking into consideration the fact that the product is instable. The reaction temperature ranges from $30°$ to $80°$ C. and reaction period of time is between 20 minutes and 3 hours.

To the thus obtained ester of 3-oxopropylmethylphosphinic acid is applied the Strecker's process. Namely, the ester is subjected to reaction in a reaction system of sodium cyanide/ammonium chloride/aqueous ammonia or of cyanic acid/aqueous ammonia or the like at $80°$ to $140°$ C. for 2 to 5 hours. After the reaction mixture is concentrated to dryness, the aminonitrile compound obtained is hydrolyzed with an acid or an alkali to obtain the desired compound of this invention, that is, D,L-2-amino-4-methylphosphinobutyric acid.

In order to isolate the present compound, the concentrated residue of the hydrolysate is extracted with alcohol to remove insoluble inorganic salts; the extract is decolored with a powdery carbon; and crystals are precipitated from a solvent system of water and alcohol. Thus, D,L-2-amino-4-methylphosphinobutyric acid can easily be obtained. Similarly, the desired compound can also be obtained easily according to the hydantoin process.

Next, this invention will be explained further in more detail by means of the following examples, which however, is not construed to limit the present invention.

EXAMPLE 1

Preparation of ethyl 3,3-diethoxypropylmethylphosphinate

Into a 100 ml. red flask was introduced 12.5 g. of acrolein, and 15 mg. of hydroquinone and 45 ml. of anhydrous ethyl alcohol were added thereto. The resulting mixture was stirred at −10° C. in a stream of nitrogen and then 13.6 g. of diethyl methylphosphonite was added dropwise thereto over 20 minutes. After stirring further for 30 minutes at the same temperature, the mixture was stirred for 2 hours at 0° C. and subsequently for 4 hours at room temperature, followed by further reaction at 70° C. for 12 hours. After the reaction mixture thus obtained was concentrated by evaporation of the ethanol under reduced pressure, the residue was subjected to distillation under reduced pressure to give a fraction boiling at 85° to 91° C./0.17 mmHg. and thus was obtained 12.2 g. of a light-yellow oil of ethyl, 3,3-diethoxypropylmethylphosphinate.

EXAMPLE 2

Preparation of ethyl 3-oxopropylmethylphosphinate

In a mixture of 15 ml. of a distilled water and 60 ml. of acetone was dissolved 6.5 g. of ethyl 3,3-diethoxypropylmethylphosphinate which had been obtained in Example 1. To the resulting mixture were added 10 mg. of hydroquinone and 0.5 ml. of a concentrated hydrochloric acid, and the mixture was stirred at 50° C. for one hour in a stream of nitrogen. After cooled to 0° C. and adjusted to pH 6 with NaHCO₃, the reaction mixture was concentrated under reduced pressure at a temperature of not more than 40° C. To the residue thus obtained was added 30 ml. of ethanol and insoluble inorganic salts were removed by filtration, followed by concentration to dryness of the filtrate to obtain 3.8 g. of a light-yellow oil of ethyl 3-oxopropylmethylphosphinate.

EXAMPLE 3

Preparation of D,L-2-amino-4-methylphosphinobutyric acid

To 2.5 g. of the ethyl 3-oxopropylmethylphosphinate which had been obtained in Example 2, there were added 1.05 g. of potassium cyanide, 0.95 g. of ammonium chloride and 7 ml. of a 28% aqueous ammonia, and the resulting mixture was subjected to reaction at 130° C. for 3 hours.

The reaction mixture was concentrated as such to dryness. After 20 ml. of a concentrated hydrochloric acid was added to the residue thus obtained, the mixture was refluxed for 6 hours under heating for hydrolysis. The reaction mixture was evaporated to dryness under reduced pressure to remove the excess amount of the hydrochloric acid. The resulting residue was treated with 25 ml. of ethanol and insoluble inorganic salts were removed by filtration. The filtrate thus obtained was evaporated to dryness, after decolorization with a carbon powder to give a light-yellow syrup. The syrup was dissolved in 3 ml. of distilled water and the resulting solution was adjusted to pH 3.0 to 3.5 with 5 N caustic soda. After addition of 8 ml. of ethanol thereto, the resulting solution was allowed to stand at low temperature to precipitate crystals, which were then collected by filtration to give 1.9 g. of white needles of D,L-2-amino-4-methylphosphinobutyric acid.

EXAMPLE 4

Preparation of D,L-2-amino-4-methylphosphinobutyric acid

In 4.5 ml. of water was dissolved the ethyl ester of 3-oxopropylmethylphosphinic acid obtained in Example 2. To the resulting solution were added 1.2 ml. of hydrocyanic acid and 11 ml. of a 28% aqueous ammonia and then the mixture was subjected to reaction at 90° C. for 1.5 hours.

Subsequently, 7 ml. of a 30% aqueous solution of sodium hydroxide was added thereto and the mixture was heated at 170° C. for 50 minutes to carry out the hydrolysis. After the reaction mixture was concentrated as such to around 5 ml. to remove the excess amount of the ammonia, the concentrate thus obtained was adjusted to pH 1 with 5 N aqueous hydrochloric acid and concentrated as such to dryness. The residue was extracted with 30 ml. of hot ethanol to remove insoluble substances. The extract was treated in the same manner as in Example 3 to obtain 2.2 g. of white needles of D,L-2-amino-4-methylphosphinobutyric acid.

We claim:

1. A process for preparing D,L-2-amino-4-methylphosphinobutyric acid represented by the formula:

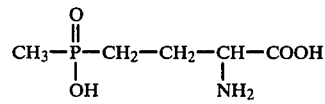

which comprises subjecting acrolein to reaction with a dialkyl methylphosphonite represented by the general formula:

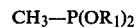

wherein R₁ means a lower-alkyl group having 1 to 5 carbon atoms, in a solvent of the general formula:

wherein R₂ means a lower-alkyl group having 1 to 5 carbon atoms, an allyl group, a phenyl group or a substituted phenyl group, to synthesize an acetal of an ester of 3-oxopropylmethylphosphinic acid represented by the general formula:

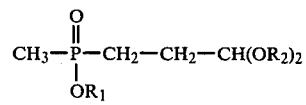

wherein R₁ and R₂ have the same meanings as defined above, respectively, and then subjecting an ester of 3-oxopropylmethylphosphinic acid, which is obtained by treating the product of the above-mentioned general formula with an acid, to the Strecker's reaction used for an amino acid synthesis.

2. A process for preparing D,L-2-amino-4-methylphosphinobutyric acid according to claim 1 wherein said reaction of a dialkyl methylphosphonite with acrolein is carried out at $-50°$ to $100°$ C., in the presence of a polymerization inhibitor in a stream of an inert gas.

3. A process for preparing D,L-2-amino-4-methylphosphinobutyric acid according to claim 1 wherein said acetal of an ester of 3-oxopropylmethylphosphinic acid is subjected to deacetalization by treating with a mineral acid or an organic acid in an aqueous solvent in the presence of a polymerization inhibitor in a stream of an inert gas.

4. A process for preparing an acetal of an ester of 3-oxopropylmethylphosphinic acid respresented by the general formula:

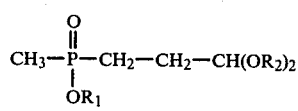

wherein $R_1$ means a lower-alkyl group having 1 to 5 carbon atoms and $R_2$ means a lower-alkyl group having 1 to 5 carbon atoms, an allyl group, a phenyl group or a substituted phenyl group, which comprises subjecting acrolein to reaction with a dialkyl methylphosphonite represented by the general formula:

$$CH_3-P(OR_1)_2$$

wherein $R_1$ has the same meaning as defined above, in a solvent of the general formula:

$$R_2OH$$

wherein $R_2$ has the same meaning as defined above.

5. A process for preparing an acetal of an ester a 3-oxopropylmethylphosphinic acid according to claim 4 wherein said reaction is carried out at $-50°$ to $100°$ C. in the presence of a polymerization inhibitor in a stream of an inert gas.

* * * * *

UNITED STATES PATENT AND TRADEMARK OFFICE
CERTIFICATE OF CORRECTION

PATENT NO. : 4,264,532
DATED : April 28, 1981
INVENTOR(S) : TAKASHI TSURUOKA et al It is certified that error appears in the above—identified patent and that said Letters Patent is hereby corrected as shown below:

Column 1, line 10, after "activities.", insert --The compound which is named herein 2-amino-4-methylphosphinobutyric acid is by the latest nomenclature named 2-amino-4-(hydroxy)(methyl)phosphinoylbutyric acid in accordance with the International Union Of Pure And Applied Chemistry, "Nomenclature Of Organic Chemistry", pages 384, 385 and 403 (1979 Edition).--.

Column 5, line 28, replace "respresented" with --represented--.

Signed and Sealed this

Eighth Day of June 1982

|SEAL|

Attest:

Attesting Officer

GERALD J. MOSSINGHOFF
Commissioner of Patents and Trademarks